(12) United States Patent
Nelson et al.

(10) Patent No.: US 9,782,308 B2
(45) Date of Patent: Oct. 10, 2017

(54) FASTENER FOR AN ABSORBENT ARTICLE

(71) Applicant: Medline Industries, Inc., Mundelein, IL (US)

(72) Inventors: Christopher Nelson, Hiram, GA (US); Jeremy Fogel, Evanston, IL (US)

(73) Assignee: Medline Industries, Inc., Mundelein, IL (US)

(*) Notice: Subject to any disclaimer, the term of this patent is extended or adjusted under 35 U.S.C. 154(b) by 0 days.

(21) Appl. No.: 15/189,687

(22) Filed: Jun. 22, 2016

(65) Prior Publication Data

US 2016/0302979 A1   Oct. 20, 2016

Related U.S. Application Data

(62) Division of application No. 14/193,084, filed on Feb. 28, 2014, now Pat. No. 9,375,367.

(51) Int. Cl.
| | | |
|---|---|---|
| A61F 13/49 | (2006.01) | |
| A61F 13/56 | (2006.01) | |
| A61F 13/62 | (2006.01) | |
| A61F 13/84 | (2006.01) | |
| A61F 13/15 | (2006.01) | |

(52) U.S. Cl.
CPC .... *A61F 13/5633* (2013.01); *A61F 13/15756* (2013.01); *A61F 13/49058* (2013.01); *A61F 13/5644* (2013.01); *A61F 13/622* (2013.01); *A61F 13/625* (2013.01); *A61F 13/627* (2013.01); *A61F 13/84* (2013.01)

(58) Field of Classification Search
CPC .... A61F 13/15756; A61F 13/49; A61F 13/56; A61F 13/5622; A61F 13/5633; A61F 13/5644; A61F 13/58; A61F 13/62; A61F 13/622; A61F 13/625; A61F 13/627; A61F 13/84
See application file for complete search history.

(56) References Cited

U.S. PATENT DOCUMENTS 688,143 A    12/1901  Windle
1,614,239 A   1/1927  Hammond
(Continued)

FOREIGN PATENT DOCUMENTS

WO   9619959 A1   7/1996
WO   9843574     10/1998
(Continued)

OTHER PUBLICATIONS

Notification of Transmittal of the International Search Report and the Written Opinion of the International Searching Authority, or the Declaration; International Patent Application No. PCT/US2015/017504, Medline Industries, Inc. (Nelson, Christopher, et al); May 1, 2015.
(Continued)

*Primary Examiner* — Kathryn E Ditmer
(74) *Attorney, Agent, or Firm* — Laubscher, Spendlove & Laubscher, P.C.

(57) ABSTRACT

An absorbent article includes front and rear portions and a fastener for connecting side edges of the front and rear portions. The fastener includes a grasping element attached to an outer surface of the fastener to provide for grasping by the wearer or caregiver. The grasping element may be formed of flexible material and may have a variety of configurations, including a tube, a flange, a tunnel or a pocket.

21 Claims, 7 Drawing Sheets

(56) References Cited

U.S. PATENT DOCUMENTS

| | | |
|---|---|---|
| 3,338,992 A | 8/1967 | Kinney |
| 3,341,394 A | 9/1967 | Kinney |
| 3,485,706 A | 12/1969 | Evans |
| 3,502,538 A | 3/1970 | Petersen |
| 3,502,763 A | 3/1970 | Hartmann |
| 3,542,615 A | 11/1970 | Dobo et al. |
| 3,612,055 A | 10/1971 | Mesek et al. |
| 3,692,618 A | 9/1972 | Carduck et al. |
| 3,802,817 A | 4/1974 | Matsuki et al. |
| 3,849,241 A | 11/1974 | Butin et al. |
| 3,860,003 A | 1/1975 | Buell |
| 3,955,575 A | 5/1976 | Okuda |
| 3,994,486 A | 11/1976 | Nystrand |
| 4,050,462 A | 9/1977 | Woon et al. |
| 4,051,853 A | 10/1977 | Egan, Jr. |
| 4,055,180 A | 10/1977 | Karami |
| 4,084,592 A | 4/1978 | Tritsch |
| 4,145,763 A | 3/1979 | Abrams et al. |
| 4,195,634 A | 4/1980 | DiSalvo et al. |
| 4,205,679 A | 6/1980 | Repke et al. |
| 4,246,900 A | 1/1981 | Schroder |
| 4,251,643 A | 2/1981 | Harada et al. |
| 4,253,461 A | 3/1981 | Strickland et al. |
| 4,296,750 A | 10/1981 | Woon et al. |
| 4,317,449 A | 3/1982 | Nowakoski |
| 4,333,466 A | 6/1982 | Matthews |
| 4,340,563 A | 7/1982 | Appel et al. |
| 4,381,781 A | 5/1983 | Sciaraffa et al. |
| 4,402,690 A | 9/1983 | Redfern |
| 4,410,324 A | 10/1983 | Sabee |
| 4,413,996 A | 11/1983 | Taylor |
| D272,190 S | 1/1984 | Sneider |
| 4,490,147 A | 12/1984 | Pierce et al. |
| 4,500,316 A | 2/1985 | Damico |
| 4,516,976 A | 5/1985 | Bell |
| 4,560,381 A | 12/1985 | Southwell |
| 4,596,568 A | 6/1986 | Flug |
| 4,610,680 A | 9/1986 | LaFleur |
| 4,610,682 A | 9/1986 | Kopp |
| 4,615,695 A | 10/1986 | Cooper |
| 4,643,932 A | 2/1987 | Daniels |
| 4,662,875 A | 5/1987 | Hirotsu et al. |
| 4,663,220 A | 5/1987 | Wisneski et al. |
| 4,670,012 A | 6/1987 | Johnson |
| 4,673,402 A | 6/1987 | Weisman et al. |
| 4,680,012 A | 7/1987 | Morley et al. |
| 4,695,278 A | 9/1987 | Lawson |
| 4,699,620 A | 10/1987 | Bernardin |
| 4,699,621 A | 10/1987 | Stevens et al. |
| 4,699,622 A | 10/1987 | Toussant et al. |
| 4,704,116 A | 11/1987 | Enloe |
| 4,710,190 A | 12/1987 | Wood et al. |
| 4,720,415 A | 1/1988 | Vander Wielen et al. |
| 4,753,649 A | 6/1988 | Pazdernik |
| 4,758,241 A | 7/1988 | Papajohn |
| 4,770,656 A | 9/1988 | Proxmire et al. |
| 4,770,657 A | 9/1988 | Ellis et al. |
| 4,798,603 A | 1/1989 | Meyer et al. |
| 4,834,735 A | 5/1989 | Alemany et al. |
| 4,834,738 A | 5/1989 | Kielpikowski et al. |
| 4,838,885 A | 6/1989 | Bernardin |
| 4,869,724 A | 9/1989 | Scripps |
| 4,883,480 A | 11/1989 | Huffman et al. |
| 4,884,323 A | 12/1989 | Provost et al. |
| 4,911,702 A | 3/1990 | O'Leary et al. |
| 4,916,005 A | 4/1990 | Loppert et al. |
| 4,936,840 A | 6/1990 | Proxmire |
| 4,938,753 A | 7/1990 | Van Gompel et al. |
| 4,938,757 A | 7/1990 | Van Gompel et al. |
| 4,940,464 A | 7/1990 | Van Gompel et al. |
| 4,963,140 A | 10/1990 | Robertson et al. |
| 4,964,860 A | 10/1990 | Gipson et al. |
| 4,988,344 A | 1/1991 | Reising et al. |
| 4,988,345 A | 1/1991 | Reising et al. |
| 5,013,382 A | 5/1991 | Nalowaniec et al. |
| 5,019,063 A | 5/1991 | Marsan et al. |
| 5,019,072 A | 5/1991 | Polski |
| 5,019,073 A | 5/1991 | Roessler et al. |
| 5,024,672 A | 6/1991 | Widlund |
| 5,026,446 A | 6/1991 | Johnson et al. |
| 5,034,008 A | 7/1991 | Breitkoph |
| 5,046,272 A | 9/1991 | Vogt et al. |
| 5,047,023 A | 9/1991 | Berg |
| 5,055,103 A | 10/1991 | Nomura et al. |
| 5,061,259 A | 10/1991 | Goldman et al. |
| 5,061,262 A | 10/1991 | Chen et al. |
| 5,062,838 A | 11/1991 | Nalowaniec et al. |
| 5,069,678 A | 12/1991 | Yamamoto et al. |
| 5,087,253 A | 2/1992 | Cooper |
| 5,104,116 A | 4/1992 | Pohjola |
| 5,106,385 A | 4/1992 | Allen et al. |
| 5,108,384 A | 4/1992 | Goulait |
| 5,128,193 A | 7/1992 | Anapol et al. |
| 5,133,707 A | 7/1992 | Rogers et al. |
| 5,134,007 A | 7/1992 | Reising et al. |
| 5,147,343 A | 9/1992 | Kellenberger |
| 5,147,347 A | 9/1992 | Huang |
| 5,149,334 A | 9/1992 | Lahman et al. |
| 5,149,335 A | 9/1992 | Kellenberger et al. |
| 5,151,092 A | 9/1992 | Buell et al. |
| 5,156,793 A | 10/1992 | Buell et al. |
| 5,156,902 A | 10/1992 | Pieper et al. |
| 5,163,932 A | 11/1992 | Nomura et al. |
| 5,176,670 A | 1/1993 | Roessler et al. |
| 5,176,671 A | 1/1993 | Roessler et al. |
| 5,188,624 A | 2/1993 | Young, Sr. et al. |
| 5,188,627 A | 2/1993 | Igaue et al. |
| 5,192,506 A | 3/1993 | Kureshy et al. |
| 5,219,646 A | 6/1993 | Gallagher et al. |
| 5,224,405 A | 7/1993 | Pohjola |
| 5,226,992 A | 7/1993 | Morman |
| 5,234,422 A | 8/1993 | Sneller et al. |
| 5,235,515 A | 8/1993 | Ungpiyakul et al. |
| 5,236,429 A | 8/1993 | Widlund |
| 5,242,436 A | 9/1993 | Weil et al. |
| 5,246,433 A | 9/1993 | Hasse et al. |
| 5,248,309 A | 9/1993 | Serbiak et al. |
| 5,263,949 A | 11/1993 | Karami et al. |
| 5,275,590 A | 1/1994 | Huffman et al. |
| 5,279,604 A | 1/1994 | Robertson et al. |
| 5,286,543 A | 2/1994 | Ungpiyakul et al. |
| 5,288,546 A | 2/1994 | Roessler et al. |
| 5,294,478 A | 3/1994 | Wanek et al. |
| 5,295,988 A | 3/1994 | Muckenfuhs et al. |
| 5,300,057 A | 4/1994 | Miller et al. |
| 5,304,161 A | 4/1994 | Noel et al. |
| 5,304,162 A | 4/1994 | Kuen |
| 5,318,555 A | 6/1994 | Siebers et al. |
| 5,320,531 A | 6/1994 | Delizo-Madamba |
| 5,326,612 A | 7/1994 | Goulait |
| 5,330,458 A | 7/1994 | Buell et al. |
| 5,344,691 A | 9/1994 | Hanschen et al. |
| 5,348,547 A | 9/1994 | Payne et al. |
| 5,350,370 A | 9/1994 | Jackson et al. |
| 5,358,500 A | 10/1994 | Lavon |
| 5,364,382 A | 11/1994 | Latimer et al. |
| 5,370,634 A | 12/1994 | Ando et al. |
| 5,370,639 A | 12/1994 | Widlund |
| 5,383,872 A | 1/1995 | Roessler et al. |
| 5,387,208 A | 2/1995 | Ashton et al. |
| 5,399,219 A | 3/1995 | Roessier et al. |
| 5,403,302 A | 4/1995 | Roessier et al. |
| 5,411,497 A | 5/1995 | Tanzer et al. |
| 5,422,172 A | 6/1995 | Wu |
| 5,423,789 A | 6/1995 | Kuen |
| 5,425,725 A | 6/1995 | Tanzer et al. |
| 5,433,715 A | 7/1995 | Tanzer et al. |
| 5,439,458 A | 8/1995 | Noel et al. |
| 5,458,592 A | 10/1995 | Abuto et al. |
| 5,460,622 A | 10/1995 | Dragoo et al. |
| 5,462,541 A | 10/1995 | Bruemmer et al. |
| 5,466,513 A | 11/1995 | Wanek et al. |
| 5,486,167 A | 1/1996 | Dragoo et al. |
| 5,489,282 A | 2/1996 | Zehner et al. |

(56) References Cited

U.S. PATENT DOCUMENTS

| | | |
|---|---|---|
| 5,490,846 A | 2/1996 | Ellis et al. |
| 5,496,298 A | 3/1996 | Kuepper et al. |
| 5,496,428 A | 3/1996 | Sageser et al. |
| 5,501,679 A | 3/1996 | Krueger et al. |
| 5,507,895 A | 4/1996 | Suekane |
| 5,509,914 A | 4/1996 | Osborn, III |
| 5,509,915 A | 4/1996 | Hanson et al. |
| 5,527,300 A | 6/1996 | Sauer |
| 5,527,302 A | 6/1996 | Endres et al. |
| 5,527,304 A | 6/1996 | Buell et al. |
| 5,527,305 A | 6/1996 | Goulait et al. |
| 5,537,722 A | 7/1996 | Niederhofer et al. |
| 5,540,796 A | 7/1996 | Fries |
| 5,549,591 A | 8/1996 | Landvogt |
| 5,549,592 A | 8/1996 | Fries et al. |
| 5,554,243 A | 9/1996 | Igaue et al. |
| 5,556,394 A | 9/1996 | Roe et al. |
| 5,562,646 A | 10/1996 | Goldman et al. |
| 5,562,650 A | 10/1996 | Everett et al. |
| 5,571,096 A | 11/1996 | Dobrin et al. |
| 5,575,782 A | 11/1996 | Hasse et al. |
| 5,591,151 A | 1/1997 | Hasse et al. |
| 5,593,399 A | 1/1997 | Tanzer et al. |
| 5,595,567 A | 1/1997 | King et al. |
| 5,595,618 A | 1/1997 | Fries et al. |
| 5,599,335 A | 2/1997 | Goldman et al. |
| 5,599,620 A | 2/1997 | Huskey |
| 5,601,542 A | 2/1997 | Melius et al. |
| 5,603,707 A | 2/1997 | Trombetta et al. |
| 5,605,735 A | 2/1997 | Zehner et al. |
| 5,624,423 A | 4/1997 | Anjur et al. |
| 5,624,428 A | 4/1997 | Sauer |
| 5,624,429 A | 4/1997 | Long et al. |
| 5,628,741 A | 5/1997 | Buell et al. |
| 5,629,063 A | 5/1997 | Gobran |
| 5,634,917 A | 6/1997 | Fujioka et al. |
| 5,647,864 A | 7/1997 | Allen et al. |
| 5,659,538 A | 8/1997 | Stuebe et al. |
| 5,660,666 A | 8/1997 | Dilnik et al. |
| 5,669,894 A | 9/1997 | Goldman et al. |
| 5,669,900 A | 9/1997 | Bullwinkel et al. |
| 5,674,216 A | 10/1997 | Buell et al. |
| 5,681,300 A | 10/1997 | Ahr et al. |
| 5,683,533 A | 11/1997 | Keighley et al. |
| 5,683,794 A | 11/1997 | Wadsworth et al. |
| 5,685,873 A | 11/1997 | Bruemmer et al. |
| 5,690,628 A | 11/1997 | Huskey et al. |
| 5,706,524 A | 1/1998 | Herrin et al. |
| 5,718,698 A | 2/1998 | Dobrin et al. |
| 5,722,127 A | 3/1998 | Coates |
| 5,735,839 A | 4/1998 | Kawaguchi et al. |
| 5,735,840 A | 4/1998 | Kline et al. |
| 5,738,669 A | 4/1998 | Suzuki et al. |
| 5,741,241 A | 4/1998 | Guidotti et al. |
| 5,745,922 A | 5/1998 | Rajala et al. |
| 5,746,731 A | 5/1998 | Hisada |
| 5,749,865 A | 5/1998 | Yamamoto et al. |
| 5,749,866 A | 5/1998 | Roe et al. |
| 5,760,080 A | 6/1998 | Wada et al. |
| 5,769,838 A | 6/1998 | Buell et al. |
| 5,772,649 A | 6/1998 | Siudzinski |
| 5,779,831 A | 7/1998 | Schmitz |
| 5,785,699 A | 7/1998 | Schmitz |
| 5,795,350 A | 8/1998 | Schmitz |
| 5,797,893 A | 8/1998 | Wada et al. |
| 5,817,400 A | 10/1998 | Chen et al. |
| 5,820,617 A | 10/1998 | Igaue et al. |
| 5,830,206 A | 11/1998 | Larsson |
| 5,843,056 A | 12/1998 | Good et al. |
| 5,843,066 A | 12/1998 | Dobrin |
| 5,843,067 A | 12/1998 | Trombetta et al. |
| 5,843,575 A | 12/1998 | Wang et al. |
| 5,849,000 A | 12/1998 | Anjur et al. |
| 5,853,402 A | 12/1998 | Faulks et al. |
| 5,855,574 A | 1/1999 | Kling et al. |
| 5,858,515 A | 1/1999 | Stokes et al. |
| 5,858,535 A | 1/1999 | Wang et al. |
| 5,860,964 A | 1/1999 | Willekens et al. |
| 5,861,074 A | 1/1999 | Wu |
| 5,865,823 A | 2/1999 | Curro |
| 5,876,392 A | 3/1999 | Hisada |
| 5,876,531 A | 3/1999 | Jacobs et al. |
| 5,895,379 A | 4/1999 | Litchholt et al. |
| 5,897,545 A | 4/1999 | Kline et al. |
| 5,897,546 A | 4/1999 | Kido et al. |
| 5,902,296 A | 5/1999 | Fluyeras |
| 5,906,604 A | 5/1999 | Ronnberg et al. |
| 5,916,206 A | 6/1999 | Otsubo et al. |
| 5,919,178 A | 7/1999 | Widlund |
| 5,926,926 A | 7/1999 | Kato |
| 5,928,212 A | 7/1999 | Kline et al. |
| 5,940,887 A | 8/1999 | Rajala et al. |
| 5,941,865 A | 8/1999 | Otsubo et al. |
| 5,948,507 A | 9/1999 | Chen et al. |
| 5,957,906 A | 9/1999 | Roe et al. |
| 5,961,506 A | 10/1999 | Guidotti et al. |
| 5,961,761 A | 10/1999 | Heindel et al. |
| 5,971,970 A | 10/1999 | Carlbark et al. |
| 5,977,430 A | 11/1999 | Roe et al. |
| 5,984,911 A | 11/1999 | Siebers et al. |
| 6,007,527 A | 12/1999 | Kawaguchi et al. |
| 6,011,196 A | 1/2000 | Wang et al. |
| 6,017,621 A | 1/2000 | Hilston et al. |
| 6,020,535 A | 2/2000 | Blenke et al. |
| 6,030,373 A | 2/2000 | Van Gompel et al. |
| 6,036,805 A | 3/2000 | McNichols |
| 6,045,543 A | 4/2000 | Pozniak et al. |
| 6,049,915 A | 4/2000 | Malowaniec |
| 6,049,916 A | 4/2000 | Rajala et al. |
| 6,051,094 A | 4/2000 | Melbye et al. |
| 6,063,067 A | 5/2000 | Takizawa et al. |
| 6,066,774 A | 5/2000 | Roe |
| 6,068,620 A | 5/2000 | Chmielewski |
| 6,075,178 A | 6/2000 | Wilhelm et al. |
| 6,077,379 A | 6/2000 | Herrin et al. |
| 6,080,909 A | 6/2000 | Osterdahl et al. |
| 6,083,212 A | 7/2000 | Kumasaka |
| 6,098,203 A | 8/2000 | Rajala et al. |
| 6,107,538 A | 8/2000 | Young et al. |
| 6,107,539 A | 8/2000 | Palumbo et al. |
| 6,117,121 A | 9/2000 | Faulks et al. |
| 6,132,411 A | 10/2000 | Huber et al. |
| 6,140,551 A | 10/2000 | Niemeyer et al. |
| 6,142,986 A | 11/2000 | Lord et al. |
| 6,156,024 A | 12/2000 | Schulte et al. |
| 6,159,584 A | 12/2000 | Eaton et al. |
| 6,179,820 B1 | 1/2001 | Fernfors |
| 6,183,587 B1 | 2/2001 | McFall et al. |
| 6,191,055 B1 | 2/2001 | Boyer, III et al. |
| 6,197,012 B1 | 3/2001 | Mishima et al. |
| 6,198,018 B1 | 3/2001 | Curro |
| 6,213,991 B1 | 4/2001 | Kling et al. |
| 6,218,593 B1 | 4/2001 | Torimae et al. |
| 6,222,091 B1 | 4/2001 | Beihoffer et al. |
| 6,224,961 B1 | 5/2001 | Hsueh et al. |
| 6,235,011 B1 | 5/2001 | O'Connell |
| 6,240,569 B1 | 6/2001 | Van Gompel et al. |
| 6,241,713 B1 | 6/2001 | Gross et al. |
| 6,255,236 B1 | 7/2001 | Cree et al. |
| 6,258,077 B1 | 7/2001 | Buell et al. |
| 6,260,211 B1 | 7/2001 | Rajala et al. |
| 6,264,643 B1 | 7/2001 | Toyoda |
| 6,287,286 B1 | 9/2001 | Akin et al. |
| 6,287,287 B1 | 9/2001 | Eisberg |
| 6,307,119 B1 | 10/2001 | Cammarota et al. |
| 6,307,120 B1 | 10/2001 | Glaug |
| 6,312,420 B1 | 11/2001 | Sasaki et al. |
| 6,315,765 B1 | 11/2001 | Datta et al. |
| 6,316,688 B1 | 11/2001 | Hammons et al. |
| 6,328,725 B2 | 12/2001 | Femfors |
| 6,359,192 B1 | 3/2002 | Schmidt et al. |
| 6,364,863 B1 | 4/2002 | Yamamoto et al. |
| 6,367,089 B2 | 4/2002 | Van Gompel et al. |
| 6,368,312 B1 | 4/2002 | Otsubo et al. |

(56) References Cited

U.S. PATENT DOCUMENTS

| | | |
|---|---|---|
| 6,369,292 B1 | 4/2002 | Strack et al. |
| 6,371,951 B1 | 4/2002 | Koczab et al. |
| 6,375,646 B1 | 4/2002 | Widlund et al. |
| 6,383,960 B1 | 5/2002 | Everett et al. |
| 6,392,116 B1 | 5/2002 | Beihoffer et al. |
| 6,394,991 B1 | 5/2002 | Takei et al. |
| 6,395,115 B1 | 5/2002 | Popp et al. |
| 6,402,730 B1 | 6/2002 | Malowaniec |
| 6,409,858 B1 | 6/2002 | Popp et al. |
| 6,413,249 B1 | 7/2002 | Turi et al. |
| 6,414,216 B1 | 7/2002 | Malowaniec |
| 6,423,046 B1 | 7/2002 | Fujioka et al. |
| 6,428,525 B1 | 8/2002 | Malowaniec |
| 6,428,526 B1 | 8/2002 | Heindel et al. |
| 6,429,352 B1 | 8/2002 | Herrlein et al. |
| 6,432,098 B1 | 8/2002 | Kline et al. |
| 6,432,243 B1 | 8/2002 | Popp et al. |
| 6,432,248 B1 | 8/2002 | Popp et al. |
| 6,437,213 B1 | 8/2002 | Schmidt et al. |
| 6,437,214 B1 | 8/2002 | Everett et al. |
| 6,440,117 B1 | 8/2002 | Itoh et al. |
| 6,447,497 B1 | 9/2002 | Olson |
| 6,447,628 B1 | 9/2002 | Couillard et al. |
| 6,454,751 B1 | 9/2002 | Olson |
| 6,455,753 B1 | 9/2002 | Giaug et al. |
| 6,458,115 B1 | 10/2002 | Lindqvist et al. |
| 6,461,343 B1 | 10/2002 | Schaefer et al. |
| 6,461,344 B1 | 10/2002 | Widlund et al. |
| 6,463,633 B1 | 10/2002 | Sangani et al. |
| 6,465,379 B1 | 10/2002 | Cook et al. |
| D465,842 S | 11/2002 | Magee et al. |
| 6,475,199 B1 | 11/2002 | Gann et al. |
| 6,476,289 B1 | 11/2002 | Buell et al. |
| 6,478,786 B1 | 11/2002 | Glaug et al. |
| 6,481,362 B2 | 11/2002 | Hietpas et al. |
| 6,494,873 B2 | 12/2002 | Karlsson et al. |
| 6,497,032 B2 | 12/2002 | Maxton et al. |
| 6,498,283 B1 | 12/2002 | Wada et al. |
| 6,500,163 B2 | 12/2002 | Rönnberg et al. |
| 6,506,394 B1 | 1/2003 | Yahiaoui et al. |
| 6,506,959 B2 | 1/2003 | Hamajima et al. |
| 6,509,513 B2 | 1/2003 | Glaug et al. |
| 6,513,221 B2 | 2/2003 | Vogt et al. |
| 6,514,187 B2 | 2/2003 | Coenen et al. |
| 6,524,294 B1 | 2/2003 | Hilston et al. |
| 6,533,879 B2 | 3/2003 | Quereshi et al. |
| 6,540,731 B2 | 4/2003 | Magnussson et al. |
| 6,544,244 B1 | 4/2003 | Glaug et al. |
| 6,551,295 B1 | 4/2003 | Schmidt et al. |
| 6,566,578 B1 | 5/2003 | Glaug et al. |
| 6,569,139 B1 | 5/2003 | Datta et al. |
| 6,570,058 B1 | 5/2003 | Fuchs et al. |
| 6,572,595 B1 | 6/2003 | Klemp et al. |
| 6,575,949 B1 | 6/2003 | Waksmundzki et al. |
| 6,575,952 B2 | 6/2003 | Kirk et al. |
| 6,579,275 B1 | 6/2003 | Pozniak et al. |
| 6,582,543 B1 | 6/2003 | Nilsson et al. |
| 6,590,136 B1 | 7/2003 | Young et al. |
| 6,595,976 B2 | 7/2003 | Shimoe ET AL. |
| 6,596,113 B2 | 7/2003 | Csida et al. |
| 6,602,238 B2 | 8/2003 | Takei et al. |
| 6,610,904 B1 | 8/2003 | Thomas et al. |
| 6,623,576 B2 | 9/2003 | Mitchell et al. |
| 6,626,881 B2 | 9/2003 | Shingu et al. |
| 6,626,882 B2 | 9/2003 | Hjorth |
| 6,630,611 B1 | 10/2003 | Malowaniec |
| 6,632,209 B1 | 10/2003 | Chmielewski |
| 6,635,041 B1 | 10/2003 | Popp et al. |
| 6,635,135 B2 | 10/2003 | Kuen et al. |
| 6,642,431 B1 | 11/2003 | Gellerstedt et al. |
| 6,645,338 B1 | 11/2003 | Sangani et al. |
| 6,646,179 B1 | 11/2003 | Melius et al. |
| 6,646,180 B1 | 11/2003 | Chmielewski |
| 6,648,870 B2 | 11/2003 | Itoh et al. |
| 6,648,871 B2 | 11/2003 | Kusibojoska et al. |
| 6,649,810 B1 | 11/2003 | Minato et al. |
| 6,664,439 B1 | 12/2003 | Arndt et al. |
| 6,669,678 B2 | 12/2003 | Hermansson et al. |
| 6,676,645 B1 | 1/2004 | Bitterhof |
| 6,689,934 B2 | 2/2004 | Dodge, II et al. |
| 6,692,477 B2 | 2/2004 | Gibbs |
| 6,700,036 B2 | 3/2004 | Thomas et al. |
| 6,702,798 B2 | 3/2004 | Christoffel et al. |
| 6,709,423 B1 | 3/2004 | Herrlein et al. |
| 6,710,225 B1 | 3/2004 | Everett et al. |
| 6,719,744 B2 | 4/2004 | Kinnear et al. |
| 6,723,035 B2 | 4/2004 | Franklin et al. |
| 6,723,892 B1 | 4/2004 | Daley et al. |
| 6,726,669 B2 | 4/2004 | Shimada et al. |
| 6,726,670 B2 | 4/2004 | Almberg et al. |
| 6,727,403 B1 | 4/2004 | Ehrnsperger et al. |
| 6,733,483 B2 | 5/2004 | Raufman et al. |
| 6,736,804 B1 | 5/2004 | Robertson et al. |
| 6,740,071 B2 | 5/2004 | Gibbs |
| 6,749,860 B2 | 6/2004 | Tyrrell et al. |
| 6,755,808 B2 | 6/2004 | Balogh et al. |
| 6,761,711 B1 | 7/2004 | Fletcher et al. |
| 6,764,479 B2 | 7/2004 | Kusibojoska et al. |
| 6,770,065 B1 | 8/2004 | Sasaki et al. |
| 6,776,316 B2 | 8/2004 | Van Eperen et al. |
| 6,780,173 B2 | 8/2004 | Mishima et al. |
| 6,780,272 B2 | 8/2004 | Wood |
| 6,790,798 B1 | 9/2004 | Suzuki et al. |
| 6,803,496 B2 | 10/2004 | Elder et al. |
| 6,838,591 B2 | 1/2005 | Waksmundzki et al. |
| 6,840,928 B2 | 1/2005 | Datta et al. |
| 6,846,374 B2 | 1/2005 | Popp et al. |
| 6,849,067 B2 | 2/2005 | Fletcher et al. |
| 6,878,223 B2 | 4/2005 | Kuen et al. |
| 6,878,647 B1 | 4/2005 | Rezai et al. |
| 6,885,451 B2 | 4/2005 | Vogt et al. |
| 6,888,043 B2 | 5/2005 | Geiser et al. |
| 6,888,044 B2 | 5/2005 | Fell et al. |
| 6,888,143 B2 | 5/2005 | Vogt et al. |
| 6,891,080 B2 | 5/2005 | Minato et al. |
| 6,904,865 B2 | 6/2005 | Klofta et al. |
| 6,911,024 B2 | 6/2005 | Kusibojoska et al. |
| 6,923,798 B2 | 8/2005 | Hedén et al. |
| 6,936,129 B2 | 8/2005 | Karami et al. |
| 6,945,968 B2 | 9/2005 | Svensson et al. |
| 6,946,585 B2 | 9/2005 | Brown |
| 6,953,452 B2 | 10/2005 | Popp et al. |
| 6,955,668 B2 | 10/2005 | Almberg et al. |
| 6,972,011 B2 | 12/2005 | Maeda et al. |
| 6,972,012 B1 | 12/2005 | Pozniak et al. |
| 6,981,968 B2 | 1/2006 | Kusibojoska et al. |
| 6,991,622 B2 | 1/2006 | Nakaoka et al. |
| 7,000,260 B2 | 2/2006 | Rajala et al. |
| 7,001,368 B2 | 2/2006 | Otsubo |
| 7,018,369 B2 | 3/2006 | Van Gompel et al. |
| 7,044,133 B2 | 5/2006 | Lohrengel et al. |
| 7,048,725 B2 | 5/2006 | Kling et al. |
| 7,060,058 B2 | 6/2006 | Otsubo et al. |
| D527,102 S | 8/2006 | Mills et al. |
| 7,087,046 B2 | 8/2006 | Van Gompel et al. |
| 7,090,667 B2 | 8/2006 | Fell et al. |
| D527,818 S | 9/2006 | Mills et al. |
| 7,156,939 B2 | 1/2007 | Vogt et al. |
| 7,163,745 B2 | 1/2007 | Mangold et al. |
| 7,166,094 B2 | 1/2007 | Glaug et al. |
| 7,172,585 B2 | 2/2007 | Sandin et al. |
| 7,175,910 B2 | 2/2007 | Ehrnsperger et al. |
| 7,195,622 B2 | 3/2007 | Lindström |
| 7,201,743 B2 | 4/2007 | Röhrl |
| 7,204,907 B2 | 4/2007 | Cree et al. |
| 7,217,261 B2 | 5/2007 | Otsubo et al. |
| 7,270,881 B2 | 9/2007 | Schmidt et al. |
| 7,285,178 B2 | 10/2007 | Mischler et al. |
| 7,314,465 B2 | 1/2008 | Van Gompel et al. |
| 7,322,967 B2 | 1/2008 | Kondo |
| 7,331,946 B2 | 2/2008 | Shimada et al. |
| 7,332,642 B2 | 2/2008 | Liu |
| 7,344,525 B2 | 3/2008 | Linker, III et al. |
| 7,347,846 B2 | 3/2008 | Hermansson et al. |

(56) References Cited

U.S. PATENT DOCUMENTS

| | | |
|---|---|---|
| 7,368,027 B2 | 5/2008 | Schneider et al. |
| 7,373,698 B2 | 5/2008 | Erdman et al. |
| 7,378,567 B2 | 5/2008 | Mangold |
| 7,378,568 B2 | 5/2008 | Thomas et al. |
| 7,387,148 B2 | 6/2008 | Vogt et al. |
| 7,396,349 B2 | 7/2008 | Van Himbergen et al. |
| 7,396,585 B2 | 7/2008 | Schmidt et al. |
| 7,402,339 B2 | 7/2008 | Schmidt et al. |
| 7,411,110 B2 | 8/2008 | Sawyer et al. |
| 7,425,242 B2 | 9/2008 | Olsson et al. |
| 7,432,413 B2 | 10/2008 | Roe et al. |
| 7,435,245 B2 | 10/2008 | Wendelstorf et al. |
| 7,438,709 B2 | 10/2008 | Karami et al. |
| 7,449,014 B2 | 11/2008 | Oba et al. |
| 7,455,665 B2 | 11/2008 | Wendelstorf et al. |
| 7,462,754 B2 | 12/2008 | Malowaniec |
| 7,462,756 B2 | 12/2008 | Malowaniec |
| 7,482,505 B2 | 1/2009 | Stupperich et al. |
| 7,488,535 B2 | 2/2009 | Ehrnsperger et al. |
| 7,524,313 B2 | 4/2009 | Kline et al. |
| 7,524,449 B2 | 4/2009 | Walsh et al. |
| 7,524,561 B2 | 4/2009 | Schmidt et al. |
| 7,527,618 B2 | 5/2009 | Benning et al. |
| 7,534,481 B2 | 5/2009 | Seth et al. |
| 7,544,628 B2 | 6/2009 | Stupperich et al. |
| 7,559,124 B2 | 7/2009 | Poulakis |
| 7,569,039 B2 | 8/2009 | Matsuda et al. |
| 7,569,041 B2 | 8/2009 | Stupperich et al. |
| 7,604,624 B2 | 10/2009 | Veith et al. |
| 7,621,901 B2 | 11/2009 | Karami |
| 7,682,349 B2 | 3/2010 | Popp et al. |
| 7,687,680 B2 | 3/2010 | Fell et al. |
| 7,695,464 B2 | 4/2010 | Fletcher et al. |
| 7,699,825 B2 | 4/2010 | Nakagawa et al. |
| 7,713,371 B2 | 5/2010 | Lohrengel et al. |
| 7,718,021 B2 | 5/2010 | Venturino et al. |
| 7,722,590 B2 | 5/2010 | Tsuji et al. |
| 7,737,324 B2 | 6/2010 | LaVon et al. |
| 7,744,576 B2 | 6/2010 | Busam et al. |
| 7,744,713 B2 | 6/2010 | Blessing et al. |
| 7,749,211 B2 | 7/2010 | Van Gompel et al. |
| 7,750,203 B2 | 7/2010 | Becker et al. |
| 7,758,558 B2 | 7/2010 | Otsubo |
| D624,696 S | 9/2010 | Hsiao |
| 7,794,442 B2 | 9/2010 | Roehrl et al. |
| 7,794,839 B2 | 9/2010 | Schmidt et al. |
| 7,807,861 B2 | 10/2010 | Molander et al. |
| 7,819,851 B2 | 10/2010 | Karlsson |
| 7,837,662 B2 | 11/2010 | Nakagawa et al. |
| 7,838,721 B2 | 11/2010 | Chen |
| 7,838,722 B2 | 11/2010 | Blessing et al. |
| 7,851,667 B2 | 12/2010 | Becker et al. |
| 7,851,669 B2 | 12/2010 | Nakagawa et al. |
| 7,857,801 B2 | 12/2010 | Hamall et al. |
| 7,863,498 B2 | 1/2011 | Roe et al. |
| 7,867,213 B2 | 1/2011 | Bandorf et al. |
| 7,906,065 B1 | 3/2011 | Brown et al. |
| 7,918,959 B2 | 4/2011 | Hornung et al. |
| 7,923,597 B2 | 4/2011 | Ponomarenko et al. |
| 7,935,299 B2 | 5/2011 | Walsh et al. |
| 7,943,537 B2 | 5/2011 | Vincent et al. |
| 7,947,865 B2 | 5/2011 | Fossum et al. |
| 7,956,236 B2 | 6/2011 | Ponomarenko et al. |
| 7,993,320 B2 | 8/2011 | Hornung et al. |
| 7,994,384 B2 | 8/2011 | Qin et al. |
| 8,016,806 B2 | 9/2011 | Hornung et al. |
| 8,017,827 B2 | 9/2011 | Hundorf et al. |
| 8,025,652 B2 | 9/2011 | Hornung et al. |
| 8,038,662 B2 | 10/2011 | Hornung et al. |
| 8,083,724 B2 | 12/2011 | Bittner et al. |
| 8,088,967 B2 | 1/2012 | Underhill et al. |
| 8,100,173 B2 | 1/2012 | Hornung et al. |
| 8,138,388 B2 | 3/2012 | Elder et al. |
| 8,142,590 B2 | 3/2012 | Rajala et al. |
| 8,148,598 B2 | 4/2012 | Tsang et al. |
| 8,152,788 B2 | 4/2012 | Beckert et al. |
| 8,158,848 B2 | 4/2012 | Swerev et al. |
| 8,162,913 B2 | 4/2012 | Goates et al. |
| 8,180,603 B2 | 5/2012 | Blessing et al. |
| 8,187,240 B2 | 5/2012 | Busam et al. |
| 8,202,390 B2 | 6/2012 | Malowaniec |
| 8,206,533 B2 | 6/2012 | Hundorf et al. |
| 8,221,372 B2 | 7/2012 | Kouno et al. |
| 8,221,379 B2 | 7/2012 | Lam et al. |
| 8,221,672 B2 | 7/2012 | Brown et al. |
| 8,231,593 B2 | 7/2012 | Nakagawa et al. |
| 8,241,263 B2 | 8/2012 | Mills |
| 8,251,967 B2 | 8/2012 | Malowaniec |
| 8,258,366 B2 | 9/2012 | Wendelstorf |
| 8,263,820 B2 | 9/2012 | Carlucci et al. |
| 8,282,617 B2 | 10/2012 | Kaneda |
| 8,303,562 B2 | 11/2012 | Hornung et al. |
| 8,319,005 B2 | 11/2012 | Becker et al. |
| 8,343,296 B2 | 1/2013 | Blessing et al. |
| 8,353,891 B2 | 1/2013 | Hornung et al. |
| 8,454,572 B2 | 6/2013 | Roe et al. |
| 8,454,782 B2 | 6/2013 | Ostertag |
| 8,466,336 B2 | 6/2013 | Carlucci et al. |
| 8,476,173 B2 | 7/2013 | Dovertie et al. |
| 8,496,637 B2 | 7/2013 | Hundorf et al. |
| 8,512,305 B2 | 8/2013 | Dziezok et al. |
| 8,518,539 B2 | 8/2013 | Meyer et al. |
| 8,552,252 B2 | 10/2013 | Hundorf et al. |
| 8,585,666 B2 | 11/2013 | Weisman et al. |
| 8,616,867 B2 | 12/2013 | Brown et al. |
| 8,622,984 B2 | 1/2014 | Rajala et al. |
| 8,663,186 B2 | 3/2014 | Lam et al. |
| 8,668,975 B2 | 3/2014 | Westwood |
| 8,672,915 B2 | 3/2014 | Kuwano et al. |
| 8,708,990 B2 | 4/2014 | Beckert et al. |
| 8,747,379 B2 | 6/2014 | Fletcher et al. |
| 8,771,249 B2 | 7/2014 | Beckert et al. |
| 8,784,398 B2 | 7/2014 | Beckert et al. |
| 8,864,733 B2 | 10/2014 | Koenig et al. |
| D716,938 S | 11/2014 | Fitter et al. |
| 8,920,399 B2 | 12/2014 | Mills et al. |
| 9,439,811 B2 | 9/2016 | Love et al. |
| D768,963 S | 10/2016 | Amrikhas et al. |
| 9,486,368 B2 | 11/2016 | Nelson |
| 2001/0023341 A1 | 9/2001 | Karami |
| 2001/0034512 A1 | 10/2001 | Karlsson et al. |
| 2001/0042584 A1 | 11/2001 | Karami et al. |
| 2002/0003024 A1 | 1/2002 | Vogt et al. |
| 2002/0045881 A1 | 4/2002 | Kusibojoska et al. |
| 2002/0062117 A1 | 5/2002 | Raufman et al. |
| 2002/0111596 A1 | 8/2002 | Fletcher et al. |
| 2002/0115969 A1 | 8/2002 | Maeda et al. |
| 2002/0123733 A1 | 9/2002 | Itoh et al. |
| 2002/0138056 A1 | 9/2002 | Kuen et al. |
| 2002/0138062 A1 | 9/2002 | Kuen et al. |
| 2002/0156441 A1 | 10/2002 | Sawyer et al. |
| 2002/0177829 A1 | 11/2002 | Fell et al. |
| 2003/0022581 A1 | 1/2003 | Tsai et al. |
| 2003/0023225 A1 | 1/2003 | Sayama |
| 2003/0055394 A1 | 3/2003 | Gibbs |
| 2003/0097113 A1 | 5/2003 | Molee |
| 2003/0100878 A1 | 5/2003 | Leak et al. |
| 2003/0105446 A1 | 6/2003 | Hutson et al. |
| 2003/0113507 A1 | 6/2003 | Niemeyer et al. |
| 2003/0119404 A1 | 6/2003 | Belau et al. |
| 2003/0199843 A1 | 10/2003 | Kato et al. |
| 2004/0044324 A1 | 3/2004 | Swenson et al. |
| 2004/0102755 A1 | 5/2004 | Morman et al. |
| 2004/0122410 A1 | 6/2004 | Itoh et al. |
| 2004/0133180 A1 | 7/2004 | Mori et al. |
| 2004/0158212 A1 | 8/2004 | Ponomarenko et al. |
| 2004/0243086 A1 | 12/2004 | Van Gompel et al. |
| 2004/0243089 A1 | 12/2004 | Veith et al. |
| 2005/0020992 A1 | 1/2005 | Van Gompel et al. |
| 2005/0027279 A1 | 2/2005 | Minato et al. |
| 2005/0075618 A1 | 4/2005 | Kenmochi et al. |
| 2005/0131378 A1 | 6/2005 | Sasaki et al. |
| 2005/0143709 A1 | 6/2005 | Lindstrom |
| 2005/0148960 A1 | 7/2005 | Price |

(56) References Cited

U.S. PATENT DOCUMENTS

| | | |
|---|---|---|
| 2005/0175269 A1 | 8/2005 | Ashton |
| 2005/0228356 A1 | 10/2005 | LaVon et al. |
| 2005/0256494 A1 | 11/2005 | Datta |
| 2005/0256496 A1 | 11/2005 | Benning et al. |
| 2005/0273067 A1 | 12/2005 | Malowaniec et al. |
| 2006/0024433 A1 | 2/2006 | Blessing et al. |
| 2006/0025733 A1 | 2/2006 | Kikuchi et al. |
| 2006/0036230 A1 | 2/2006 | Mills et al. |
| 2006/0058772 A1 | 3/2006 | Karami |
| 2006/0069379 A1 | 3/2006 | Van Gompel et al. |
| 2006/0121811 A1 | 6/2006 | Mangold et al. |
| 2006/0135923 A1 | 6/2006 | Boggs et al. |
| 2006/0135928 A1 | 6/2006 | Karlsson et al. |
| 2006/0135932 A1 | 6/2006 | Abuto et al. |
| 2006/0155254 A1 | 7/2006 | Sanz et al. |
| 2006/0167424 A1 | 7/2006 | Chang et al. |
| 2006/0184149 A1 | 8/2006 | Kasai et al. |
| 2006/0195068 A1 | 8/2006 | Lawando |
| 2006/0241560 A1 | 10/2006 | Chang et al. |
| 2006/0247596 A1 | 11/2006 | Van Dyke |
| 2006/0258250 A1 | 11/2006 | Mangold et al. |
| 2006/0276765 A1 | 12/2006 | Swerev et al. |
| 2006/0282053 A1 | 12/2006 | Rohrl |
| 2007/0000987 A1 | 1/2007 | Karlsson |
| 2007/0016155 A1 | 1/2007 | Chang et al. |
| 2007/0038199 A1 | 2/2007 | Erdman et al. |
| 2007/0044903 A1 | 3/2007 | Wisneski et al. |
| 2007/0048497 A1 | 3/2007 | Zhou et al. |
| 2007/0049892 A1 | 3/2007 | Lord et al. |
| 2007/0066950 A1 | 3/2007 | Nelson |
| 2007/0073260 A1 | 3/2007 | Roe |
| 2007/0073262 A1 | 3/2007 | Babusik et al. |
| 2007/0208317 A1 | 9/2007 | Krautkramer et al. |
| 2007/0239131 A1 | 10/2007 | Harmansson et al. |
| 2007/0255246 A1 | 11/2007 | Schneider |
| 2007/0293833 A1 | 12/2007 | Wennerback |
| 2007/0293835 A1 | 12/2007 | Roehrl et al. |
| 2008/0026178 A1 | 1/2008 | Stupperich et al. |
| 2008/0051747 A1 | 2/2008 | Cohen |
| 2008/0103414 A1 | 5/2008 | Song |
| 2008/0108964 A1 | 5/2008 | Edwall |
| 2008/0125735 A1 | 5/2008 | Busam et al. |
| 2008/0134487 A1 | 6/2008 | Hartono |
| 2008/0161767 A1 | 7/2008 | Sandin et al. |
| 2008/0208152 A1 | 8/2008 | Eckstein et al. |
| 2008/0249493 A1 | 10/2008 | Kobayashi et al. |
| 2008/0281286 A1 | 11/2008 | Petersen |
| 2008/0287897 A1 | 11/2008 | Guzman Reyes et al. |
| 2008/0287898 A1 | 11/2008 | Guzman Reyes et al. |
| 2008/0287899 A1 | 11/2008 | Morrell-Schwartz et al. |
| 2008/0312618 A1 | 12/2008 | Hundorf et al. |
| 2008/0312628 A1 | 12/2008 | Hundorf et al. |
| 2008/0312631 A1 | 12/2008 | Okuda |
| 2009/0143757 A1 | 6/2009 | Hornung et al. |
| 2009/0177176 A1 | 7/2009 | Saito |
| 2009/0198205 A1 | 8/2009 | Malowaniec et al. |
| 2009/0275911 A1 | 11/2009 | Hormung et al. |
| 2009/0299322 A1 | 12/2009 | Faulks et al. |
| 2009/0312736 A1 | 12/2009 | Schroer, Jr. et al. |
| 2009/0326499 A1 | 12/2009 | Veith et al. |
| 2009/0326503 A1 | 12/2009 | Lakso et al. |
| 2010/0051170 A1 | 3/2010 | Nakakado |
| 2010/0063468 A1 | 3/2010 | Lehto et al. |
| 2010/0065199 A1 | 3/2010 | Hormung et al. |
| 2010/0076390 A1 | 3/2010 | Norrby et al. |
| 2010/0108251 A1 | 5/2010 | Malowaniec |
| 2010/0168705 A1 | 7/2010 | Stabelfeldt et al. |
| 2010/0198178 A1 | 8/2010 | Litvay |
| 2010/0285286 A1 | 11/2010 | Middlesworth |
| 2010/0292663 A1 | 11/2010 | Lavon et al. |
| 2010/0318055 A1 | 12/2010 | Hornung et al. |
| 2011/0071488 A1 | 3/2011 | Kuwano et al. |
| 2011/0077609 A1 | 3/2011 | Kuwano et al. |
| 2011/0098668 A1 | 4/2011 | Thorson et al. |
| 2011/0123775 A1 | 5/2011 | Westwood |
| 2011/0130275 A1 | 6/2011 | Weisman et al. |
| 2011/0146892 A1 | 6/2011 | Ostertag |
| 2011/0160692 A1 | 6/2011 | Wilkes et al. |
| 2011/0208140 A1 | 8/2011 | Roe et al. |
| 2011/0208142 A1 | 8/2011 | Roe et al. |
| 2012/0028777 A1 | 2/2012 | Knecht |
| 2012/0053552 A1 | 3/2012 | Van Gompel et al. |
| 2012/0065607 A1 | 3/2012 | Konig et al. |
| 2012/0165777 A1 | 6/2012 | Beckert et al. |
| 2012/0172828 A1 | 7/2012 | Koenig et al. |
| 2012/0310193 A1 | 12/2012 | Ostertag |
| 2013/0144245 A1 | 6/2013 | Roe |
| 2013/0211365 A1 | 8/2013 | Rajala et al. |
| 2013/0261589 A1 | 10/2013 | Fujkawa et al. |
| 2013/0281957 A1 | 10/2013 | Fritz et al. |
| 2014/0046286 A1 | 2/2014 | Homann et al. |
| 2015/0011958 A1 | 1/2015 | Yoshioka |
| 2015/0297421 A1 | 10/2015 | Nelson |

FOREIGN PATENT DOCUMENTS

| | | |
|---|---|---|
| WO | 9923985 A1 | 5/1999 |
| WO | 2006017718 A1 | 2/2006 |

OTHER PUBLICATIONS

Supplementary European Search Report; European Patent Application No. EP15755486, Medline Industries, Inc.; Jul. 17, 2017.

FASTENER FOR AN ABSORBENT ARTICLE

CROSS-REFERENCE TO RELATED APPLICATIONS

This application is a division of U.S. patent application Ser. No. 14/193,084 filed Feb. 28, 2014.

FIELD OF THE INVENTION

The present invention relates generally to absorbent articles and, in particular, to the use of fastening tab features for absorbent articles that provide for grasping by the wearer or caregiver.

BACKGROUND OF THE INVENTION

Millions of people of all ages suffer from incontinence of the bowel or bladder. Whether an infant, adult, or elderly person, the underlying cause of incontinence varies but the method of treatment typically involves use of absorbent article products. Adult incontinent briefs, disposable diapers and underpads can alleviate some of the emotional and physical discomfort of incontinence by absorbing and containing liquid and other discharges from the human body to prevent body and clothing soiling.

Typical absorbent articles include a topsheet facing the wearer that permits fluid exudates to pass through and a backsheet that prevents the exudates from escaping from the absorbent article. Much advancement has been made in the art since the introduction of the disposable absorbent article, as shown, for example, in applicant's co-pending U.S. patent application Ser. No. 13/832,965, which is incorporated by reference herein. However, a fastening tab features that provide for grasping by the wearer or caregiver, while minimizing the risk of accidental opening the fastening tab because of shear with clothing or bed sheets.

Current absorbent article products include features or construction of fastening tape tabs that facilitate the opening of the tab. This is important for easy application of the product, and because caregivers are often wearing gloves during patient care. One fastening method includes a fold-over of the "peel" edge, which usually results in a sharp corner, as shown for example in U.S. Pat. No. 4,090,516. Another fastening method employs a wavy edge often along with a non-glued or non-adhesive region, as shown for example in U.S. Pat. No. 8,251,970.

Both embodiments can easily be caught in the wearer's clothing or bed sheets causing the absorbent article to accidentally open.

The present invention was developed in order to overcome these and other drawbacks by providing absorbent articles with fastening features that can be easily grasped but do not become caught in the wearers clothing or bed sheets.

BRIEF DESCRIPTION OF THE FIGURES

Other objects and advantages of the invention will become apparent from a study of the following specification when viewed in light of the accompanying drawing, in which.

DETAILED DESCRIPTION

Absorbent articles as described herein generally include a moisture-pervious inner layer, an absorbent layer, and a moisture-impervious outer layer. Although the remainder of the description will be specifically directed to adult incontinence articles, such as disposable diapers, it is to be understood that the embodiments may also be implemented using other absorbent articles and that the properties and uses described below apply to these other absorbent articles as well. Throughout this application, the terms absorbent article and diaper are used interchangeably. However, it should be understood that the term diaper is intended to include other absorbent articles, such as training pants, incontinence pads, etc., as would be understood by one of ordinary skill in the art.

Embodiments of the invention are now described in detail. Referring to the drawings, like numbers indicate like parts throughout the views. As used in the description herein and throughout the claims, the following terms take the meanings explicitly associated herein, unless the context clearly dictates otherwise: the meaning of "a," "an," and "the" includes plural reference, the meaning of "in" includes "in" and "on." Relational terms such as first and second, top and bottom, proximal and distal, and the like may be used solely to distinguish one entity or action from another entity or action without necessarily requiring or implying any actual such relationship or order between such entities or actions.

Figure 1:
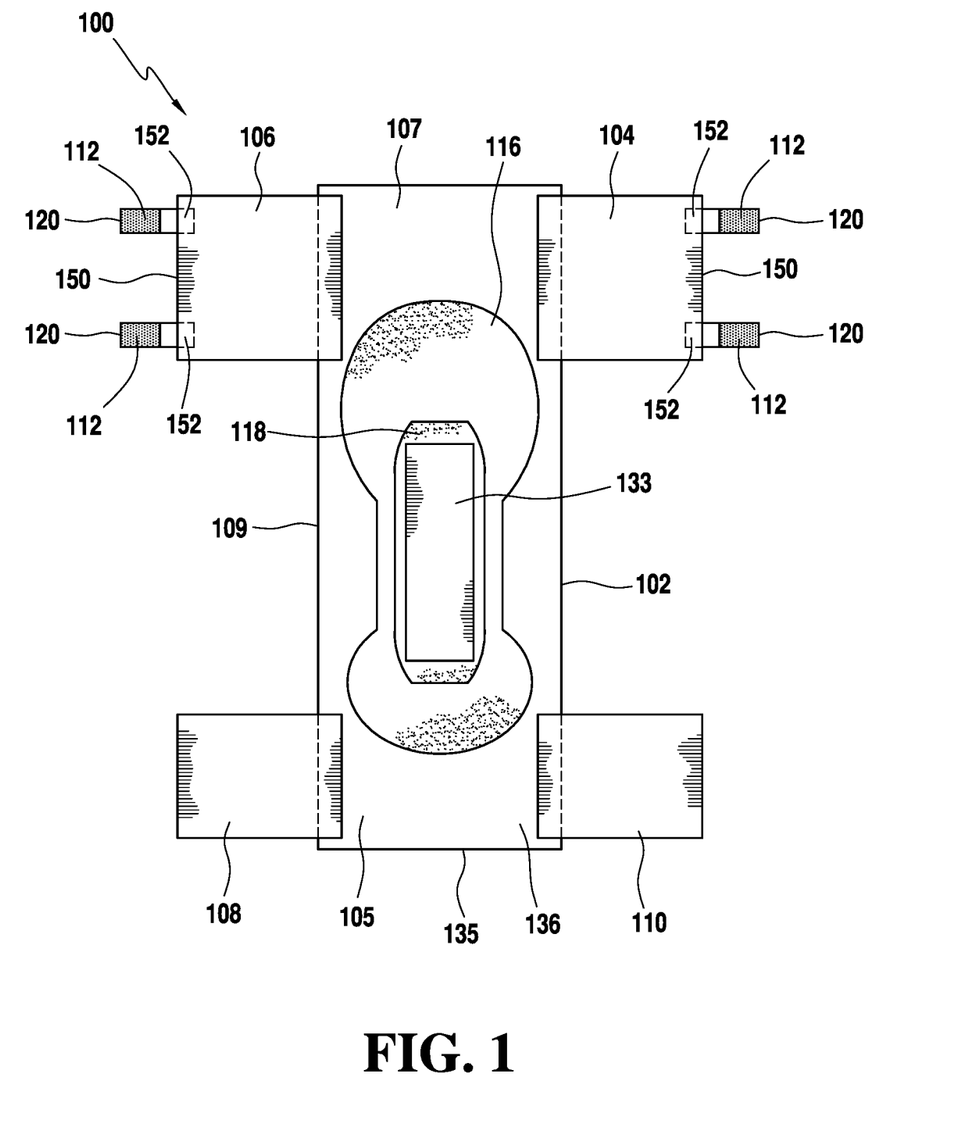
FIG. 1 is a top plan view of an absorbent article in a substantially flat un-contracted position according to an embodiment of the invention.
Figure 2:
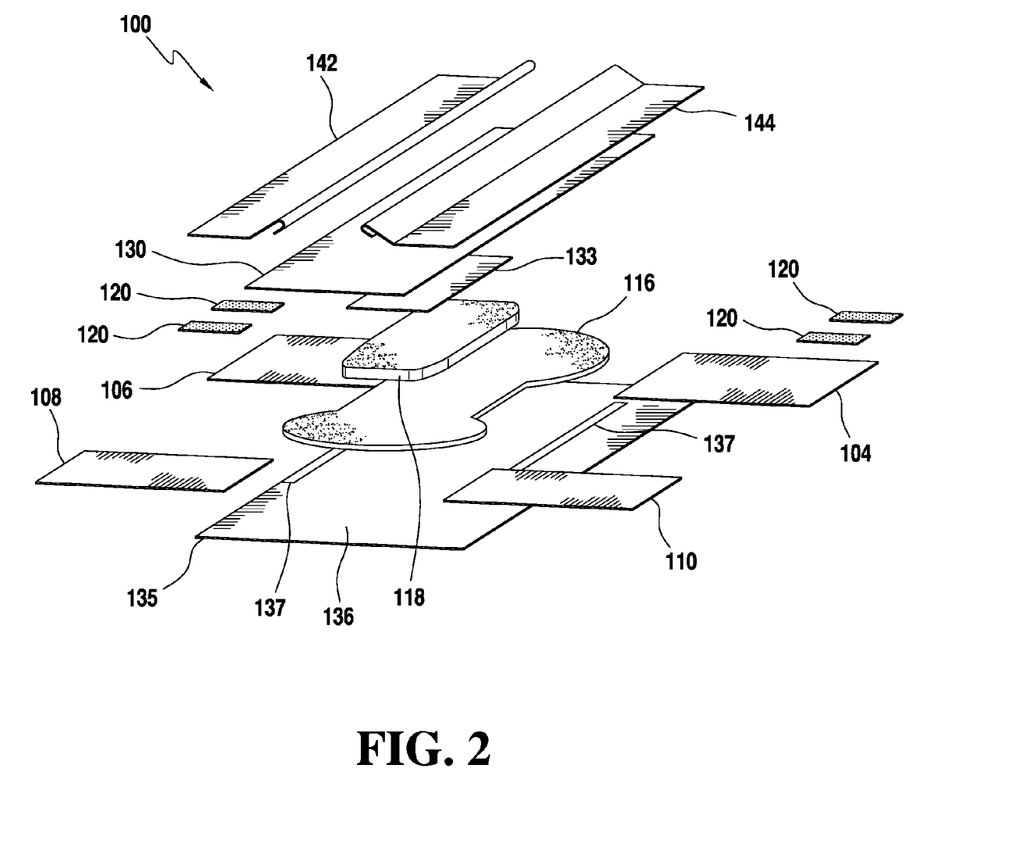
FIG. 2 is an exploded perspective view of the absorbent article of FIG. 1, again in a substantially flat un-contracted position.

FIGS. 1 and 2 illustrate an exemplary non-limiting general embodiment of an absorbent article 100. FIG. 1 illustrates a plan view of the absorbent article 100 in a substantially flat un-contracted state. As shown in these figures, the absorbent article 100 generally consists of several layers, including an inner layer, an absorbent layer, and an outer layer. The inner layer faces a wearer and contacts the skin of the wearer when the absorbent article 100 is secured to the wearer. The inner layer may comprise a topsheet that is composed of a moisture-pervious fabric suitable to allow bodily discharge to pass through the inner layer and be absorbed by the absorbent layer. Non-limiting examples of materials suitable to form the topsheet include polypropylene, polyethylene, polyester, materials having hydrophobic properties, combinations thereof and/or the like. Additionally, the topsheet can be treated with a hydrophilic finish to improve pass through of liquids to diaper layers beneath the inner layer. Non-limiting examples of suitable hydrophilic finishes include stearic acid, melamine-based chemicals, fluorocarbon chemicals, and silicon based chemicals.

The plan view of FIG. 1 is shown from the top or patient contacting side of the absorbent article. The topsheet (130) and other components have been removed for clarity. FIG. 2 is an exploded perspective view of the absorbent article 100. Again, the article 100 is shown in a substantially flat un-contracted state with certain items removed for clarity.

As shown in FIG. 1, an embodiment of the absorbent article 100 comprises a chassis 102. The chassis 102 includes a front waist region 105, a back waist region 107, and a crotch region 109 that is disposed longitudinally between the front and back waist regions 105 and 107. The front waist region 105 and the back waist region 107 generally comprise those portions of the absorbent article 100 which, when worn, encircle the waist of the wearer. The crotch region 109 is that portion of the absorbent article 100 which, when the absorbent article 100 is worn, is generally positioned between the legs of the wearer.

The chassis 102 has a shape such that its outer perimeter is rectangular or at least substantially rectangular in the illustrative embodiment of the absorbent article 100. In other embodiment, there may be portions of the chassis that are shaped and/or removed, such as in the crotch region 109, for example, resulting in a narrower crotch region portion 109 to provide a contoured fit between the legs. Still other embodiments have different shaped chassis, such as hourglass shapes, T-shapes, and the like.

Rear side panels 104, 106 are coupled to and may extend from the back waist region 105. The disposable article may further include front side panels 108, 110 that are coupled to and may extend from the front waist region 105. The back region 107 is generally positioned against the back of the user. The front region 105 is generally positioned against the front of the user. The rear side panels 104, 106 are configured to wrap around a wearer's waist from back to front, extending from each side of the back waist region 105. The front side panels 108, 110 are configured to wrap around a wearer's waist from front to back. In this manner, rear side panel 106 can be connected to front side panel 108 and rear side panel 104 can be connected to front side panel 110 to couple the front region 105 to the back region 107. In this embodiment there are four side panels 104, 106, 108, 110. However, it should be recognized that other embodiments may be configured with more or fewer side panels. In particular, rear side panels 104, 106 may connect directly to an outside surface of front waist region 105 rather than to front side panels 108, 110.

The side panels may attach to the chassis 102 in a variety of manners as would be apparent to one of skill in the art. For example, as described in applicant's co-pending U.S. patent application Ser. No. 13/832,965 (U.S. Pat. App. Pub. 2013/0345657), which is incorporated herein by reference. Alternatively, one or more of the side panels may be integrally formed, in whole or in part, with a backsheet 135 or topsheet 130 of the absorbent article. The backsheet 135 will have an outside surface 134 facing away from the patient wearing the absorbent article and an inside surface 136 facing toward the patient.

The rear side panels 104, 106 may also include fasteners 120. Fasteners 120 may comprise adhesive tape, hook and loop, snaps or any other appropriate fasteners as would be understood by one of ordinary skill in the art. As shown in the illustrative embodiment, rear side panel 104, 106 includes two fasteners 120. In a preferred embodiment, fasteners 120 can be configured to operatively couple rear side panels 104, 106 to a front region 105 of the diaper chassis 102. The fasteners 120 extend laterally from side edges 150 of the rear side panels 104, 106. The fasteners may overlap in a portion 152 to provide an adhesive area for attaching the fasteners to the side panels. Alternative, fasteners 120 may also engage front side panels 108, 110 to attach rear side panels 104, 106, respectively. While FIG. 1 depicts rear side panels 104, 106 as including two fasteners 120, in some embodiments, more or fewer fasteners may be used. While FIG. 1 depicts fasteners 120 sized and shaped a particular way, in other embodiments, fasteners 120 can be a different size and/or shape. Alternatively, the front side panels 108, 110 may include fasteners in additions to, or in place of, the fasteners 120 attached to rear side panels 104, 106.

In another embodiment, the front region 105 and/or front panels 108, 110 may include added or modified features to reinforce or increase the affinity to the fastening device. Additionally, features may be employed to allow adhesive fasteners to be attached and detached from the fastening region multiple times. Those skilled in the art will recognize that there are multiple approaches to doing so via modification of the base material as well as additions of various materials. For example, fasteners 120 may incorporate the hook component 112 of a hook-and-loop closure and portions of the front region 105 and/or front panels 108, 110 may be comprise a corresponding loop component. The surface of front region 105 and/or front panels 108, 110 may be treated to increase or decrease the affinity for the hook components. Alternatively, separate loop component material may be adhered to the surface of the front region 105 and/or front panels 108, 110.

Referring again FIGS. 1 and 2, embodiments of the absorbent article 100 include an absorbent layer. The absorbent layer may comprise an acquisition and/or distribution ("A/D") layer 133, a first absorbent core 116, and a second absorbent core 118. The liquid acquisition and/or distribution layers serves to rapidly acquire and then distribute acquired liquid to an absorbent core for retention. To achieve rapid acquisition and distribution, these layers often include cellulosic fibers. These layers can include cross-linked cellulosic fibers to impart bulk and resilience to the layer, and wood pulp fibers to increase the wicking of liquid within the layer and to facilitate distribution of the liquid throughout the layer and ultimately to another layer, such as a storage layer, that is in liquid communication with the distribution layer.

Figure 3:
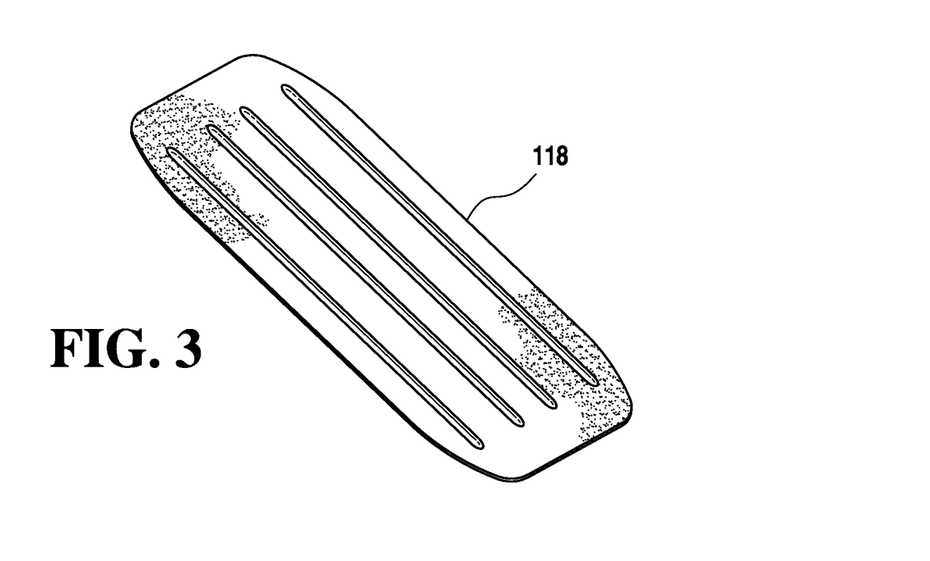
FIG. 3 is a perspective view of a second absorbent core of the absorbent article depicted in FIG. 1.
Figure 4:
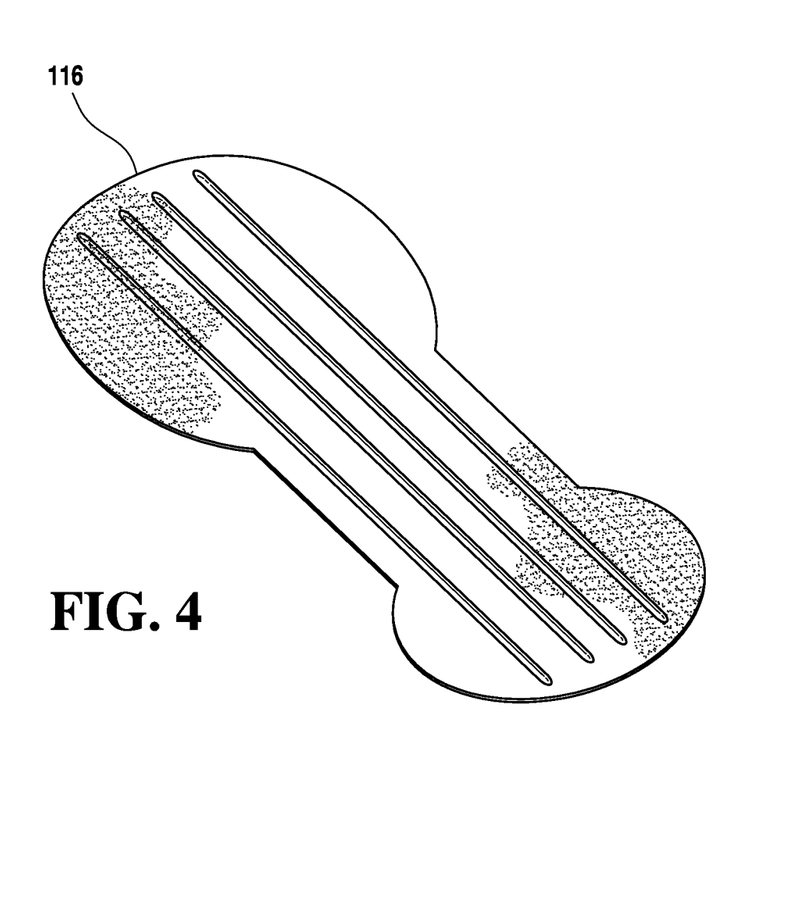
FIG. 4 is a perspective view of a first absorbent core of the absorbent article depicted in FIG. 1.

FIG. 3 is a perspective view of a top (facing towards wearer) of the second core 118, and FIG. 4 is a perspective view of a bottom side (facing away from a wearer) of the first core 116. Each of the first core 116 and second core 118 can be composed of similar material, and can be shaped depending on the size of the absorbent article, and whether it is intended for use by infants, children and/or adults. By way of example, and as shown in FIGS. 3 and 4, first core 116 can be larger and substantially hourglass shaped, whereas second core 118 can be smaller, relative to first core 116, and can be substantially rectangular shaped. In this manner, the absorbent article can include a large surface area of coverage provided by the first core 116, and the increased absorbency provided by the second core 118, without the additional bulk of a second core having the same size as the first core.

First core 116 is shown having an embossed bottom and second core 118 is shown having an embossed top. The embossed top of second core 118 and the embossed bottom of first core 116 provide increased longitudinal flow while reducing lateral flow, and, in this manner, reducing leakage. Said another way, the embossed top of second core 118 and the embossed bottom of first core 116 allows fluid to move longitudinally towards the front and the back of a wearer, as opposed to towards the legs of a wearer.

Each of the first core 116 and the second core 118 may be composed of any materials suitable for absorbing the fluids and discharge including, but not limited to, a fibrous material (e.g., fluffed wood pulp), a super absorbent polymer ("SAP"), or the combination of SAP and fibrous material. The SAP can be natural or synthetic and may be biodegradable. Non-limiting examples of SAP include polymers based on acrylate(s) such as sodium acrylate, potassium acrylate, and/or an alkyl acrylate(s) (e.g., methyl acrylate, ethyl acrylate, propyl acrylate, butyl acrylate, and hexyl acrylate). The absorbency of the diaper may vary depending upon whether it is intended for use by infants, children and/or adults.

While FIGS. 3 and 4 depict the first core 116 having an embossed bottom, and the second core 118 having an embossed top, in some embodiments, an absorbent article can have only a single core with no embossing, a single core with embossing on both, and/or other combinations of one or two cores each with embossing on one, both, or neither side. While the figures show absorbent articles include one or two cores, in some embodiments, absorbent articles can include more or fewer cores.

FIGS. 3 and 4 depict embossing as including four spaced apart embossing "lines," in some embodiments. However, a core can include more or fewer embossing lines. In some embodiments, embossing lines can be adjacent one another, or can be a combination of adjacent and space apart embossing line. In this manner, the different combinations of embossing lines can define an embossing pattern. While FIGS. 3 and 4 depict embossing substantially along the entire width and length of each respective core, in some embodiments a core can have embossing substantially along an entire width and/or length, and/or a portion of a width and/or length.

In embodiments of the invention, the first 116 and second 118 cores may be created with or without the use of super absorbent polymer (SAP). While some literature indicates that the presence of SAP in a diaper used for urine testing is considered benign, manufacturing diapers without SAP for the benefit of accuracy is contemplated by the present invention and may be considered beneficial.

Returning to FIGS. 1 and 2, the absorbent article 100 may further include a set of leak guards and/or a set leg cuffs 142, 144, both known to those of ordinary skill in the art.

Additionally, the exemplary absorbent article includes an outer layer or backsheet 135 and elastic bands 137. The elastic bands 137 can by used to gather the leg of the article around the user's leg, improving the fit of the absorbent article 100 and can improve the comfort of the wearer. Elastic bands and other elastic materials may be used at other places in the absorbent article in order to improve the fit and/or fluid retention of the article.

Figures 5, 6, 7, 8, 9, 10:
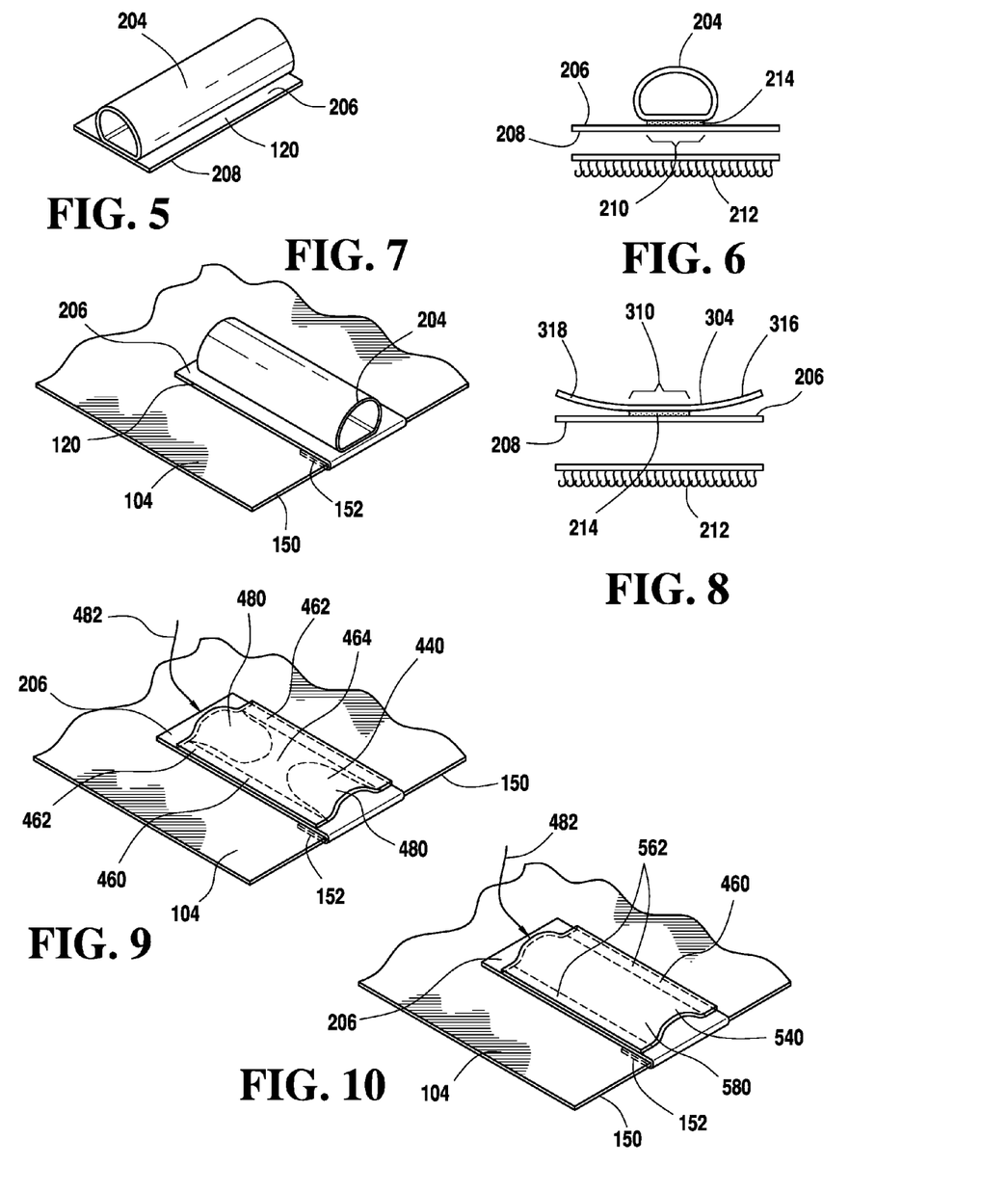
FIG. 5 is a perspective view of an embodiment of a grasping element attached to a fastener of the absorbent article.
FIG. 6 is a partially exploded end-view of the embodiment illustrated in FIG. 5.
FIG. 7 is a perspective view of the embodiment illustrated in FIG. 5 showing the fastener attached to a side part of the absorbent article.
FIG. 8 is a partially exploded end-view of an embodiment of the grasping element.
FIG. 9 is a perspective view of an embodiment of the grasping element showing the fastener attached to a side part of the absorbent article.
FIG. 10 is a perspective view of an embodiment of the grasping element showing the fastener attached to a side part of the absorbent article.

As illustrated in FIGS. 5-14, fasteners 120 may include a grasping element that provide for grasping by the wearer or caregiver. In an embodiment shown in FIGS. 5-6, the fastener 120 may have an outer portion 206, which faces away from the wearer when the article is in use, and an inner portion 208, which faces toward the wearer when the article is in use. A grasping element, in this embodiment a flexible tube 204, is affixed to the outer portion 206 of the fastener 120. As shown in FIG. 6, the hook structures 212 of a hook and loop type fasteners may be attached to a length of the inner portion 208 of the fastener.

The tube 204 is attached to the fastener 120 along a region 210 that is narrower than the width of the fastener. In an embodiment of the invention, the region of attachment is less than 50% of the width of the fastener. Alternatively, the region of attachment may be narrower, extending across 5-45% of the fastener width. The tube 204 may be attached using an adhesive 214, which may be applied continuously or in an intermittent manner to the outer portion 206 of the fastening tape 120, such that a narrow strip of adhesive 214 is present along the centerline of the fastener 120. The tube 204 acts as a gripping surface that may be grasped by the wearer or caregiver to release a fastener once applied to the surface of an absorbent article, such as the outer surface of front side panel 108, 110.

FIG. 7 shows a fastener 120 in a folded position prior to use. The fastener is attached to an outside surface of side panel 104 at an attachment region 152. The fastener is then folded over the lateral edge 150 of the side panel 104 and folded flat against an inside surface of the side panel. The tube 204 is also folded flat against the outer portion 206 of the fastener. In further embodiments, the hooks 212 may engage the inside surface of the side panel to hold the fastener in this folded position. During the process of putting the article on the wearer, the tube 204 is grasped and pulled to extend the fastener for use in side panel to another portion of the article.

The grasping element is not limited to a tube configuration show in FIGS. 5-7. For example, as shown in FIG. 8, a ribbon 304 or other similar material can be used in place of the tube construction and attached along a region 310 that is narrower than the fastener 120 and the ribbon 304. This results in two flanges 316, 318 that extend from the fastener and may be grasped individually or together by the user or wearer.

Referring now to FIG. 9, in an additional embodiment, the fastener 120 includes an outer layer 440 of material. The material 440 may be a nonwoven material, elastomeric strip, plastic or poly film layer or other appropriate material. The outer layer 440 is preferably attached to the outer portion 206 of the fastener 120 over a specific pattern 460. The pattern 460 of attachment may be accomplished using hot melt adhesive, ultra sonic bonding or similar heat and pressure bonding. The pattern of attachment 460 is formed to create at least one finger pocket 480. To lift the fastener 120 away from the absorbent article the wearer or caregiver inserts a finger into the pocket 480 (as shown by arrow 482) and gently pulls the fastener away from an absorbent article.

As shown in FIG. 9, the attachment pattern 460 may be formed of sections 462 extending length-wise along edges of the fastener and one or more sections 464 extending width-wise across the fastener 120 to form individual pockets 480.

Figure 11:
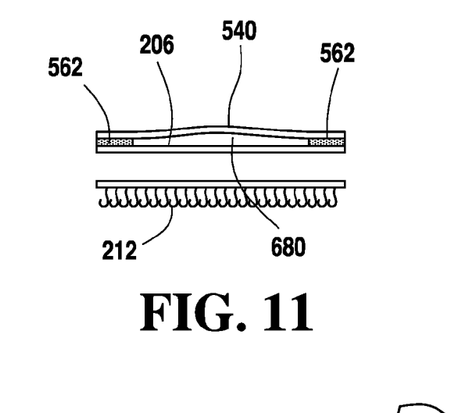
FIG. 11 is a partially exploded end-view of an embodiment of the grasping element.
Figure 12:
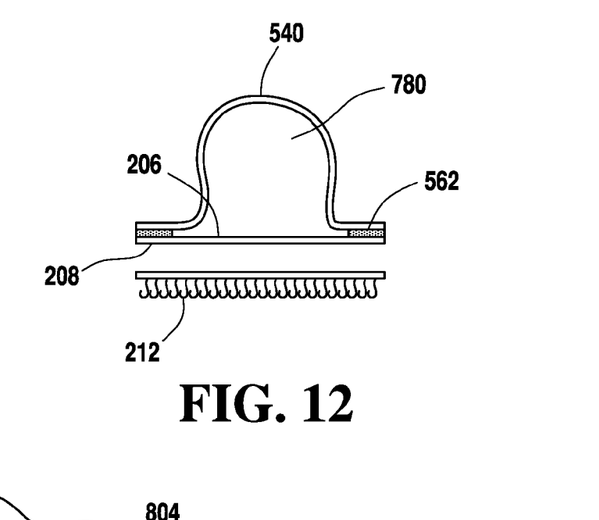
FIG. 12 is a partially exploded end-view of an embodiment of the grasping element.

Alternatively, as shown in FIG. 10, the attachment pattern 460 may comprise only sections 562 extending length-wise along edges of the fastener such that a the outer layer of material 540 is attached to form a tunnel 580, into which the wearer or caregiver inserts a finger (as shown by arrow 482). The outer layer of material 540 may be attached, as shown in FIG. 11, such that it is substantially parallel to the fastener outer portion 206 or only slightly bowed outward to form a shallow arch or tunnel. Alternatively, as shown in FIG. 12, the outer layer of material may be substantially wider that the fastener 120 such that the material forms a more open tunnel 780.

Figure 13:
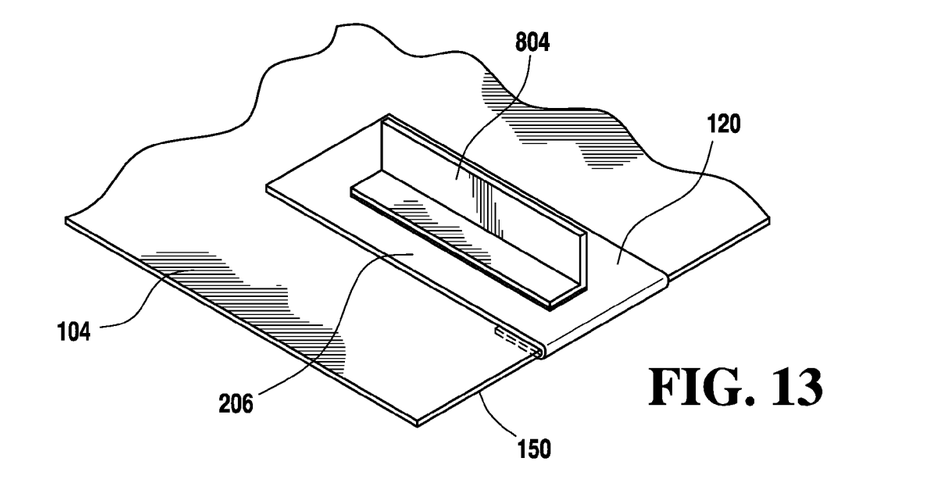
FIG. 13 is a perspective view of an embodiment of the grasping element showing the fastener attached to a side part of the absorbent article.
Figure 14:
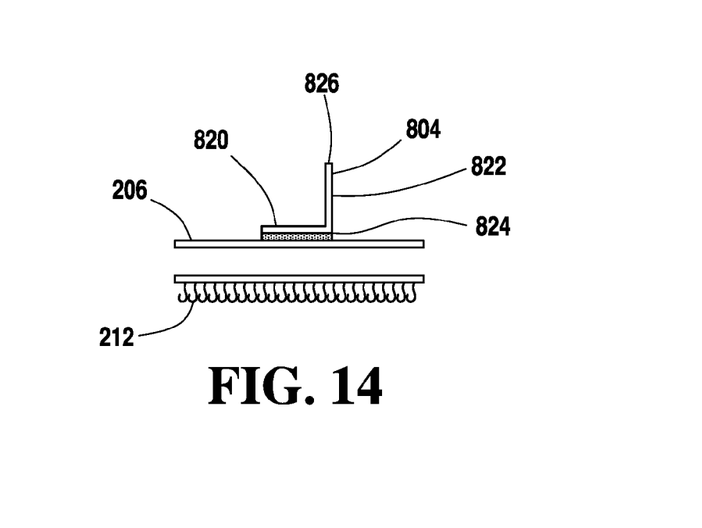
FIG. 14 is a partially exploded end-view of the embodiment illustrated in FIG. 13.

FIG. 13 shows a further embodiment of the invention in which a flexible tab 804 is attached to an outer portion 206 of the fastener 120. As shown in FIG. 14, an inner portion 208 of the fastener 120 includes hook structures 212 of hook and loop type fasteners known in the art. A base portion 820 of the tab 804 extends substantially parallel to the fastener and is affixed to the outer portion 206 of the fastener using a narrow pattern 810 of adhesive or other bonding. An extension portion 822 of the tab 804 is bent at a hinge 824 so that the extension portion extends upwardly from the fastener. The free end 826 of the tab 804 may be grasped by the wearer or caregiver to release a fastening tab once applied to the surface of the absorbent article.

Figure 15:
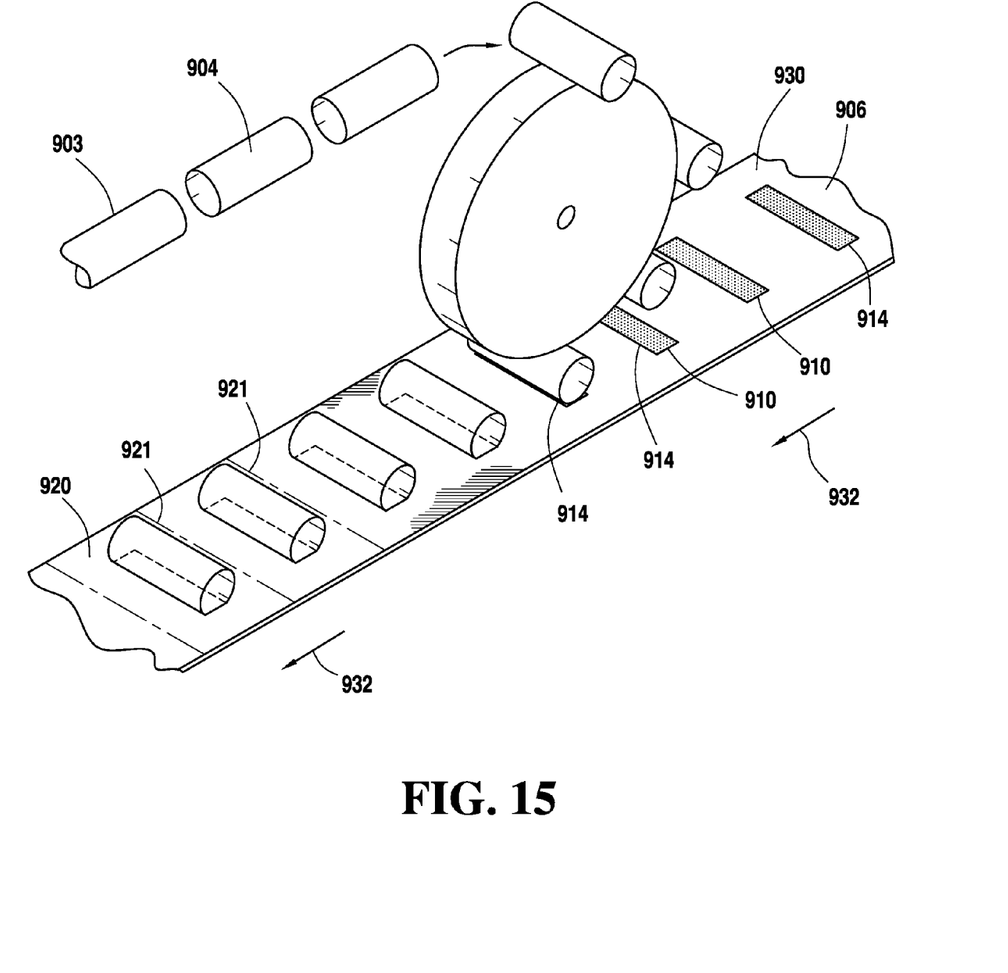
FIG. 15 is a representative diagram illustrating steps in an embodiment of a manufacturing process for manufacturing the fastener and grasping element of FIGS. 5-7.

FIG. 15 illustrates an exemplary method of a manufacturing process for the embodiment shown in FIGS. 5-7. A web of fastener material 930 passes in a first direction 932. A section of hooks for a hook-and-loop fastener is applied across a portion of the lower portion of the material (not shown). An adhesive 914 may be applied in an intermittent manner to transverse sections 910 of the-outer portion 906 of the fastener material 930. A continuous flexible tube 903 is fed into the process. The tube 203 is severed into individual tube sections 904 that are shorter than the cross-direction width of the fastener material. The tube sections 904 are turned 90 degrees and placed transversely on the web of fastening material at sections corresponding to the adhesive 914 such that the tube sections 904 adhere to the fastening material 930 at intervals. This activity may be performed while the fastening material 930 is a continuous web.

Alternatively, the adhesive may be applied continuously to the flexible tube 903 and the tube may be severed into tube sections 904 and turned 90 degrees and placed upon the outer portion 906 fastening material 930. In this alternative, the adhesive would not be applied directly to the fastening material.

Following adhesion of the tube sections, the fastening material may be severed into discrete fasteners 920 along transverse lines 921. These fasteners may then be attached to the side panels 104, 106. The fastening material may be severed at this stage of the process or may be severed at the point in the process that it is attached to the side panels.

Figure 16:
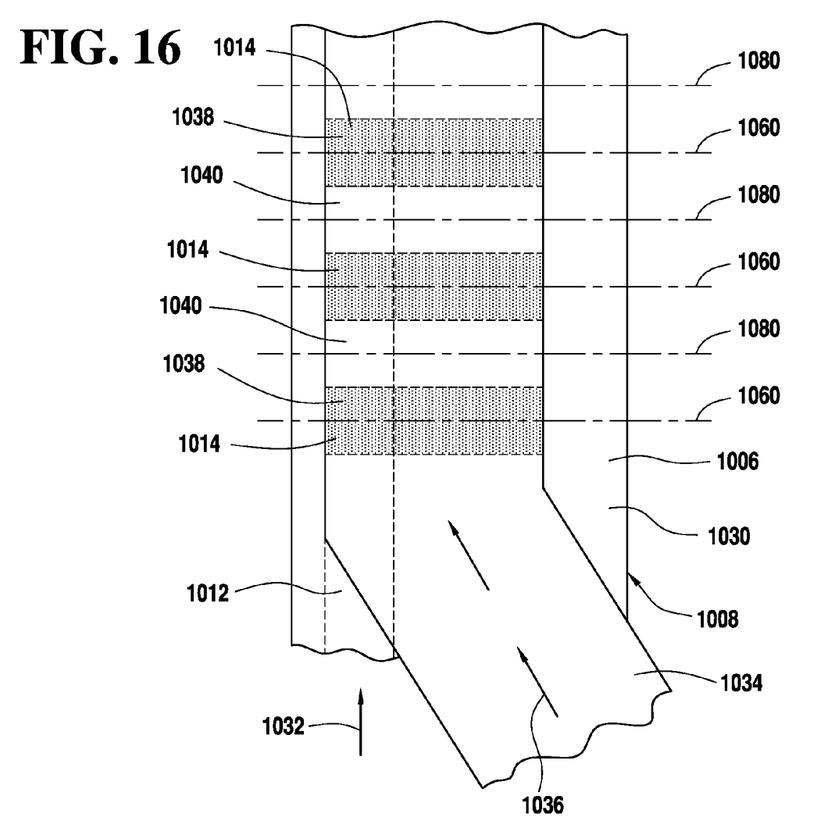
FIGS. 16-17 are representative diagrams illustrating steps in an embodiment of a manufacturing process for manufacturing the fastener and grasping element of FIGS. 13-14.
Figure 17:
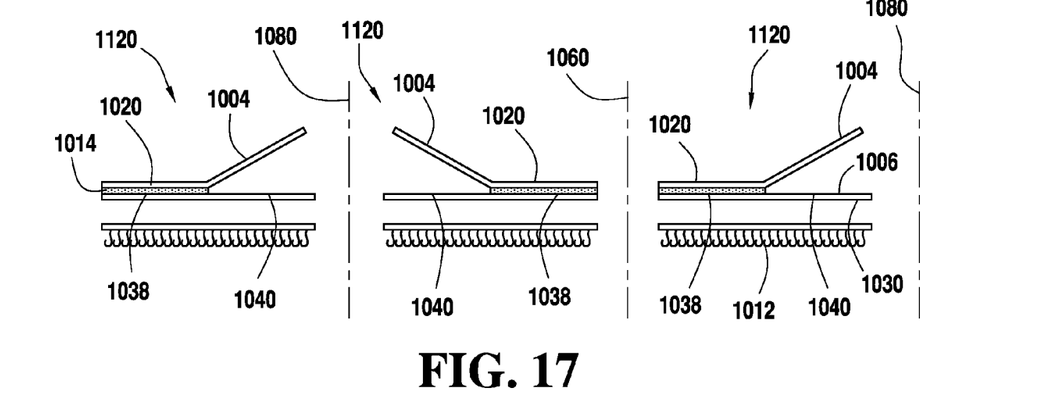

Because the tube 903 may be accelerated or decelerated to match the spacing (cut width) of the fasteners 920, there is no limitation on the fed-in length relative to the final cut length of the fasteners. Furthermore, utilizing different tube widths or diameters can provide various dimensions of gripping area for a given tape construction. Additionally, the grasping element is not limited to a tube configuration. A ribbon can be used in place of the tube construction, resulting in two flanges that can be used for more readily grasping the fastening tab. This embodiment, as well as other versions, will require registration of the web leading to the cutting and placing applicator FIGS. 16-17 show an exemplary method of a manufacturing process for the embodiments illustrated in FIGS. 13-14. A web of fastener material 1030 having an upper side 1006 and a lower side 1008 passes in a first direction 1032. A section of hooks 1012 for a hook-and-loop fastener is applied across a portion of the lower side 1008 of the material 1030. Adhesive 1014 may be applied in an intermittent manner to transverse sections of upper side 1006 of the fastener material 1030. A web of flexible flange material 1034 passes in a second direction 1036 and is realigned to be parallel to the fastener material 1030 and brought into contact with the fastener material over the transverse adhesive sections 2014. Accordingly, the application of an adhesive 1014 creates a pattern that is phased to create alternating adhered 1038 and non-adhered 1040 portions of the flange material 1034. The flange material 1034 may be narrower than the fastener material 1030 such that the flange material extends only part way across the flange material.

The resulting layup of materials may then be cut along first cut lines 1060 that pass through the non-adhered sections 1040 and along second cut lines 1080 that pass through the adhered sections 1038. The pattern of alternating adhesive and cuts results a plurality of fasteners 1120 with alternating fasteners having flexible tabs 1004 arranged in "mirror image" about the first cut line 1060 and bonded portions 1020 mirrored about a second cut line 1080. The resulting fasteners may then be attached to the side panels 104, 106. The fastening material may be severed at this stage of the process or may be severed at the point in the process that it is attached to the side panels.

What is claimed is:

1. An absorbent article comprising:
a moisture-impervious outer layer;
an inner layer substantially co-extensive with the outer layer;
a filler interposed between the inner layer and the outer layer;
a rear portion having a rear side panel with a longitudinally extending side edge, the rear portion comprising a fastener attached to the rear side panel; and
a front portion comprising a fastener attachment area on an outside surface of the front portion, wherein the attachment area is adapted to engage the fastener;
wherein the fastener comprises:
a first portion that overlaps the rear side panel of the rear portion;
a second portion that extends laterally beyond the longitudinally extending side edge, the second portion having a length that extends in a lateral direction and a width perpendicular to the length and further having an upper surface and a lower surface;
a grasping element comprising a first end and a second end, the grasping element further comprising a first finger pocket with an opening at the first end and a second finger pocket with an opening at the second end; and
an attachment zone where the grasping element is attached to the second portion upper surface, wherein the attachment zone extends length-wise along edges of the fastener second portion and extends width-wise across the fastener second portion in spaced relation to the grasping element first and second ends to form the first and second finger pockets.

2. The absorbent article of claim 1, wherein the grasping element comprises a flexible material.

3. The absorbent article of claim 2, wherein the flexible material comprises nonwoven material.

4. The absorbent article of claim 2, wherein the flexible material comprises an elastomeric material.

5. The absorbent article of claim 2, wherein the flexible material comprises a polymer film.

6. The absorbent article of claim 1, wherein the first finger pocket comprises a first axis extending along a center of the first finger pocket, and the first finger pocket axis is generally parallel to the length of the fastener second portion.

7. The absorbent article of claim 2, wherein the second finger pocket comprises a second axis extending along a center of the second finger pocket, and the second finger pocket axis is generally parallel to the length of the fastener second portion.

8. The absorbent article of claim 1, wherein the fastener attachment zone comprises an adhesive.

9. The absorbent article of claim 1, wherein the fastener attachment zone comprises an ultrasonic bond.

10. The absorbent article of claim 1, wherein the fastener attachment zone comprises a heat and pressure bond.

11. An absorbent article comprising:
a moisture-impervious outer layer;
an inner layer substantially co-extensive with the outer layer;
a filler interposed between the inner layer and the outer layer;
a rear portion having a rear side panel with a longitudinally extending side edge;
a fastener attached to the rear side panel and having a length that extends in a lateral direction and a width perpendicular to the length, the fastener comprising:
  a base layer having an outer surface that faces away from the wearer when the article is in use and an inner surface that faces toward the wearer when the article is in use;
  an engagement element attached to the inner surface of the base layer at a first attachment area; and
  a grasping element attached to the outer surface of the base layer at a second attachment area, wherein the second attachment area overlaps with the first attachment area; and
a front portion comprising a fastener attachment area on an outside surface of the front portion, wherein the attachment area is adapted to engage the fastener, and wherein the grasping element comprises:
  a first end and a second end;
  a first finger pocket with an opening at the first end and a second finger pocket with an opening at the second end; and
  an attachment zone where the grasping element is attached to the base layer outer surface, wherein the attachment zone extends length-wise along edges of the fastener and extends width-wise across the fastener in spaced relation to the grasping element first and second ends to form the first and second finger pockets.

12. The absorbent article of claim 11, wherein the engagement element comprises a hook portion of a hook-and-loop fastener.

13. The absorbent article of claim 11, wherein the front portion fastener attachment area comprises a loop portion of a hook-and-loop fastener.

14. The absorbent article of claim 11, wherein a width of the first finger pocket opening is narrower than the fastener width.

15. An absorbent article comprising:
a moisture-impervious outer layer;
an inner layer substantially co-extensive with the outer layer;
a filler interposed between the inner layer and the outer layer;
a rear portion having a rear side panel with a longitudinally extending side edge;
a fastener attached to the rear side panel, the fastener comprising:
  a base layer having an outer surface that faces away from the wearer when the article is in use, an inner surface that faces toward the wearer when the article is in use, a length extending between a first end and a second end, and a width extending between a first edge and a second edge;
  an engagement element attached to the inner surface of the base layer; and
  a grasping element attached to the outer surface of the base layer; and
a front portion comprising a fastener attachment area on an outside surface of the front portion, wherein the attachment area is adapted to engage the fastener, and wherein the grasping element comprises:
  a flexible material having a length extending between a first end and a second end and a width extending between a first edge and a second edge;
  a first attachment zone extending length-wise along the fastener first edge and securing the first edge of the flexible material to the base layer outer surface;
  a second attachment zone extending length-wise along the fastener second edge and securing the second edge of the flexible material to the base layer outer surface; and
  a tunnel formed by the grasping element between the first attachment zone and the second attachment zone, the tunnel comprising an opening at the flexible material first end and an opening at the flexible material second end wherein a length of the tunnel between the flexible material first end and the flexible material second end is greater than the width of the flexible material, wherein a user inserts a finger into the tunnel to grip the grasping element to release the fastener.

16. The absorbent article of claim 15, wherein the grasping element further comprises a third attachment zone extending width-wise across the fastener between the flexible material first end and second end and securing a lateral portion of the flexible material to the base layer outer surface.

17. The absorbent article of claim 16, wherein the first, second and third attachment zones attach the flexible material to the base layer outer surface to form a first finger pocket.

18. The absorbent article of claim 17, wherein the first, second and third attachment zones attach the flexible material to the base layer outer surface to form first and second finger pockets.

19. The absorbent article of claim 17, wherein a width of the opening at the first end of the flexible material is less than the width of the base layer.

20. The absorbent article of claim 15, wherein a width of the flexible material is greater than the width of the base layer such that the tunnel extends away from the outer surface of the base layer.

21. The absorbent article of claim 20, wherein the tunnel is folded against the base layer outer surface prior to use.

* * * * *